United States Patent [19]
Grove et al.

[11] Patent Number: 5,743,901
[45] Date of Patent: Apr. 28, 1998

[54] HIGH FLUENCE DIODE LASER DEVICE AND METHOD FOR THE FABRICATION AND USE THEREOF

[75] Inventors: Robert E. Grove, Pleasanton; James Z. Holtz, Livermore, both of Calif.

[73] Assignee: Star Medical Technologies, Inc., Pleasanton, Calif.

[21] Appl. No.: 648,212

[22] Filed: May 15, 1996

[51] Int. Cl.⁶ .................................................. A61N 5/06
[52] U.S. Cl. ........................ 606/9; 606/10; 372/72; 372/75
[58] Field of Search ........................... 606/9, 10, 11, 606/12, 14, 15, 16, 17, 18; 372/69, 70, 72, 75

[56] References Cited

U.S. PATENT DOCUMENTS

| | | | |
|---|---|---|---|
| 4,357,704 | 11/1982 | Koechner | 372/72 |
| 4,822,335 | 4/1989 | Kawai et al. | 606/10 X |
| 5,259,380 | 11/1993 | Mendes et al. | 606/9 X |
| 5,309,457 | 5/1994 | Minch | 372/69 X |
| 5,323,414 | 6/1994 | Baird et al. | 372/75 |
| 5,358,503 | 10/1994 | Bertwell et al. | 606/9 X |
| 5,521,936 | 5/1996 | Irwin | 372/75 |
| 5,548,608 | 8/1996 | Zhang | 372/75 |
| 5,616,140 | 4/1997 | Prescott | 606/10 |
| 5,627,850 | 5/1997 | Irwin et al. | 372/75 X |

*Primary Examiner*—Jennifer Bahr
*Assistant Examiner*—Sonya Harris-Ogugua
*Attorney, Agent, or Firm*—Wolf, Greenfield & Sacks, P.C.

[57] ABSTRACT

A high fluence diode laser device is provided which achieves high fluence by carefully designing the mount for the diode bars so as to permit high power and long pulse operation with little temperature rise in the diode lasers; providing a microlens array in front of the diode array to improve brightness; and utilizing a non-imaging (i.e., without lenses) optical condenser between the microlens array and the target to efficiently transmit light energy from the diode array to a smaller target area.

19 Claims, 1 Drawing Sheet

HIGH FLUENCE DIODE LASER DEVICE AND METHOD FOR THE FABRICATION AND USE THEREOF

FIELD OF THE INVENTION

This invention relates to diode laser devices and more particularly to a diode laser device designed to provide high fluence over a relatively large area. The invention also relates to methods for the fabrication and use of the high fluence diode laser device.

BACKGROUND OF THE INVENTION

Diode lasers are finding increasing use in a variety of medical, industrial and other applications. In particular, diode lasers are often used in medical applications to selectively destroy specific target tissue or other substances in the human body, including treatment for various dermatological conditions. In many of these applications, the laser light is selectively absorbed by naturally occurring chromophores such as melanin or hemoglobin (blood). In particular, in the near infrared (IR) region (700 to 1100 nm), the absorption coefficient of melanin, hemoglobin, and other naturally occurring chromophores is much lower than in the shorter wavelength visible region and the scattering coefficient of tissue is often much lower than in the visible region. Thus, near IR light can penetrate more deeply into tissue and interact with structures containing the chromophores which structures could not be reached by light of a shorter wavelength.

However, lower absorption and scattering coefficients in the near IR region mean that the fluence necessary to produce a clinical effect in this region is often an order of magnitude or more higher than in the visible region. This has been experimentally confirmed when it has been shown that fluences of at least 10 J/cm$^2$, and in some cases up to 100 J/cm$^2$ or more, are required to achieve certain desired clinical effects with IR light, particularly where the target absorbers are melanin or hemoglobin. In addition, these fluence values must be maintained over an area of greater than about 0.4 cm$^2$ in order to avoid a significant reduction in the local fluence in the tissue due to lateral beam spreading, thus eliminating the option of obtaining high fluence merely by directing the available energy to a very small spot. The combined requirements for high fluence and a substantial illumination area mean that the laser source must generally be capable of delivering from 4 to 40 Joules, and for some applications even more. Further, for a structure to be selectively heated, the energy must be delivered in a short enough time so that the heat is reasonably localized in the vicinity of the target structure. Small structures (i.e. approximately 1 micrometer in size) can be directly heated with a pulse duration in the order of 1 microsecond. Larger structures can be targeted effectively using longer duration pulses. For example, structures of approximately 300 μm in size, such as blood vessels or melanized layers, can be effectively heated using a pulse duration of up to 30 milliseconds. Still larger structures, such as veins which are 500 μm in size or larger, can be effectively heated with pulse durations of up to 100 milliseconds.

While diode lasers operating for example in the near IR wavelength region offer attractive features for medical applications, including small size and efficient operation, such lasers have not heretofore been used in applications requiring the delivery of high fluences in pulse durations of 100 milliseconds or less because of the inherent difficulties in achieving the pulse energy and fluence requirements. This is because, due to the very short relaxation times of the upper level, diode lasers can only store energy for a small fraction of a nanosecond. For this reason, the general approach to achieving high fluence pulsed light has been to use other types of lasers which are capable of storing energy, such as ruby, Nd:YAG, alexandrite, and other solid state lasers.

Another reason why diode lasers have not been used previously for high energy/fluence applications is that individual diode lasers, because of their small size, can only be operated at a maximum power level of about 1 watt per laser emitter. Higher power operation causes excessive temperature rise in the diode junction, significantly reducing life time. This power level corresponds to a delivered energy of only one mJ/ms. As a result, the attainment of energies from 4 to 40 Joules would require a very large number of individual emitters.

To provide higher output power/energy using diode lasers, individual emitters are often arrayed on a single monolithic structure called a bar (typically about 1 cm in length, 0.01 cm thick and 0.05 cm deep), containing 15 to 100 individual emitters arrayed along the 1 cm length of the bar. When operated at pulse durations of 250 microseconds or less, such bars have produced up to 200 watts of peak power. However, to achieve reasonable life, these bars are typically rated and operated at 50 watts of peak power. Such bars, operating with a duty factor of up to 20%, are used for the pumping of solid state lasers, particularly Nd:YAG. The bars are typically specified to operate with pulse durations of 250 microseconds or shorter and are mounted in such a way as to allow high average power operation of the diode bar.

However, in order to produce a pulse energy of 4 to 40 Joules using diode laser bars of the type discussed above operating at their designed power of 50 watts per bar and operating with a pulse duration of 250 microseconds or less, from 320 to 3,200 bars, depending on energy required, would be necessary. Such a large number of bars would make a commercial device prohibitively expensive. In addition, the size of an array consisting of such a large number of bars using standard packaging would be from 30 to 300 cm$^2$ in size. Because each individual diode facet typically produces a beam with a divergence of 10° to 40°, it is not possible (because of brightness limitations) to use imaging optics directly to reduce the beam's size by more than about a factor of 10, and hence, it is not possible to achieve a fluence of greater than 4 J/cm$^2$ over an approximately 1 cm$^2$ area with simple imaging optics. The use of more bars increases the total energy available, but increases the source area correspondingly, and thus does not result in higher fluence capability.

While diodes designed to operate continuous wave (cw) could be used to obtain longer pulses, these cw bars are typically limited to 10–15 watts of peak power. Thus, even with a 30-millisecond pulse duration, the energy output from a cw bar is no greater than 0.3 to 0.45 Joules per bar. To produce 4 to 40 Joules in 30 ms or less using standard arrays of cw bars would, therefore, require 9 to 90 bars or more. While the cost of a system comprising as many as 90 bars might not be excessive, the issue of brightness would still preclude the construction of a high-fluence system. This is because standard packages of cw bars and arrays are designed to accommodate the average power produced in cw operation. As such, bars are packaged either individually or in arrays with widely spaced bars (typically approximately 2 mm on centers). Because of the large number of bars required to achieve high-pulse energy and the inability to effectively couple the energy to produce a high fluence, developers have not attempted to use diode lasers for applications requiring a fluence of greater than 4 J/cm$^2$ and a pulse of less than 30 ms over an area of greater than 0.4 cm$^2$.

A need therefore exists for a practical system capable of generating fluences in the range of 10 to 100 J/cm$^2$ over areas of greater than 0.4 cm$^2$ and at pulse durations of less than 100 milliseconds and preferably less than 30 milliseconds. To achieve this, several things are necessary. First, individual bars must be operated at power levels of greater than 30 watts for long pulse durations to achieve sufficient energy from a reasonably small number of bars. Second, that pulse energy must be concentrated effectively into an area of appropriate size (i.e. an area small enough to achieve the desired fluence but large enough to avoid significant reduction in the local fluence applied to the tissue due to lateral beam spreading). Further, to achieve 10 to 100 J/cm$^2$, the product of the brightness and the pulse duration needs to be increased by a factor of 8 to 80 from that available with conventional diode arrays capable of producing 500 watts/cm$^2$ and operating with a 250 microsecond pulse.

SUMMARY OF THE INVENTION

In accordance with the above, this invention provides a high fluence diode laser device which is capable of achieving the objectives indicated above by combining at least three factors which have not heretofore been combined. First, the diode mount is designed to permit high power and long pulse operation with modest temperature rise in the diode lasers; second, an optical/microlens array is added in front of the diode array to improve array brightness; and third, a non-imaging (i.e. without lenses) optical condenser is introduced between the microlens array and the target to efficiently transmit the energy from the diode array into a smaller target area.

More specifically, the diode laser device of this invention includes at least one diode laser array having a plurality of diode laser bars mounted with spacers between the bars formed of a material having both high thermal conductivity and high thermal capacity. The bars are mounted so as to be spaced by an amount adequate to avoid significant thermal interaction between bars. A microlens or other appropriate optical array is mounted to receive light energy from the diode bars and to reduce the divergence of such light energy. A non-imaging condenser is mounted to receive light energy passing through the microlens array and to channel such energy to a smaller area for increased fluence. The non-imaging condenser preferably has a truncated pyramid-like shape, with light energy entering the large rectangular end and exiting a smaller rectangular end. The output area of the condenser typically has a generally square shape, and the outlet from the condenser is preferably applied directly to the target. For preferred embodiments, the output area of the condenser is greater than 0.5 cm$^2$. The condenser may be a hollow non-imaging condenser or may be a glass total internal reflecting condenser. The bars or arrays of the bars are preferably mounted at angles to each other along an arc having a center at the point where the sides of the condenser converge.

The microlens array may be formed of a single glass fiber adjacent each bar and positioned to have light energy from the bar pass through the side of the fiber. For some embodiments, the microlens fibers are shaped or have radial refractive index gradients to further reduce divergence of light outputted therefrom. Alternatively, the microlens array maybe a monolithic one- or two-dimensional sequence of "lenslets" formed in or on a translucent material, such "lenslets" reducing the divergence from individual emitters of the diode array.

The spacing between bars in the arrays is by a distance corresponding roughly to one-half the square root of the diffusivity of the material between the diode bars (the spacers) and the pulse duration. The spacer material's thermal figure of merit is the square root of the material's thermal conductivity times the thermal heat capacity of the material. Suitable spacer materials include beryllium oxide and copper.

For certain medical applications, and in particular medical applications involving treatment of deep blood vessels, diode lasers operating in the 700–1100 nm wavelength band are preferred, with diode lasers in the 750 nm to 950 nm being most preferred. In particular, the diode laser device discussed above can be utilized to treat selected dermatological conditions by aiming the laser device to direct light energy to at least a portion of a patient's body having the selected dermatological condition and operating the diode laser bars to produce a pulse output, with the pulses having a duration of 1 ms to 100 ms and a fluence at the body surface of 10 to 100 J/cm$^2$.

The invention also involves a method for forming a high fluence diode laser device which comprises the steps of providing at least one diode array having a plurality of diode laser bars mounted with spacers between bars formed of a material having both high thermal conductivity and high thermal capacity, the bars being mounted so as to be spaced by an amount adequate to prevent significant thermal interaction between bars; (b) mounting a microlens array to receive light energy from the diode bars and to reduce the divergence of light energy outputted therefrom, and Ⓒ mounting a non-imaging condenser to receive light energy passing through the microlens array and to channel such energy to a small area for increased fluence.

The foregoing and other objects, features, and advantages of the invention will be apparent from the following, more particular, description of a preferred embodiment of the invention as illustrated in the accompanying drawings.

IN THE DRAWINGS

DETAILED DESCRIPTION

Figures 1, 2:
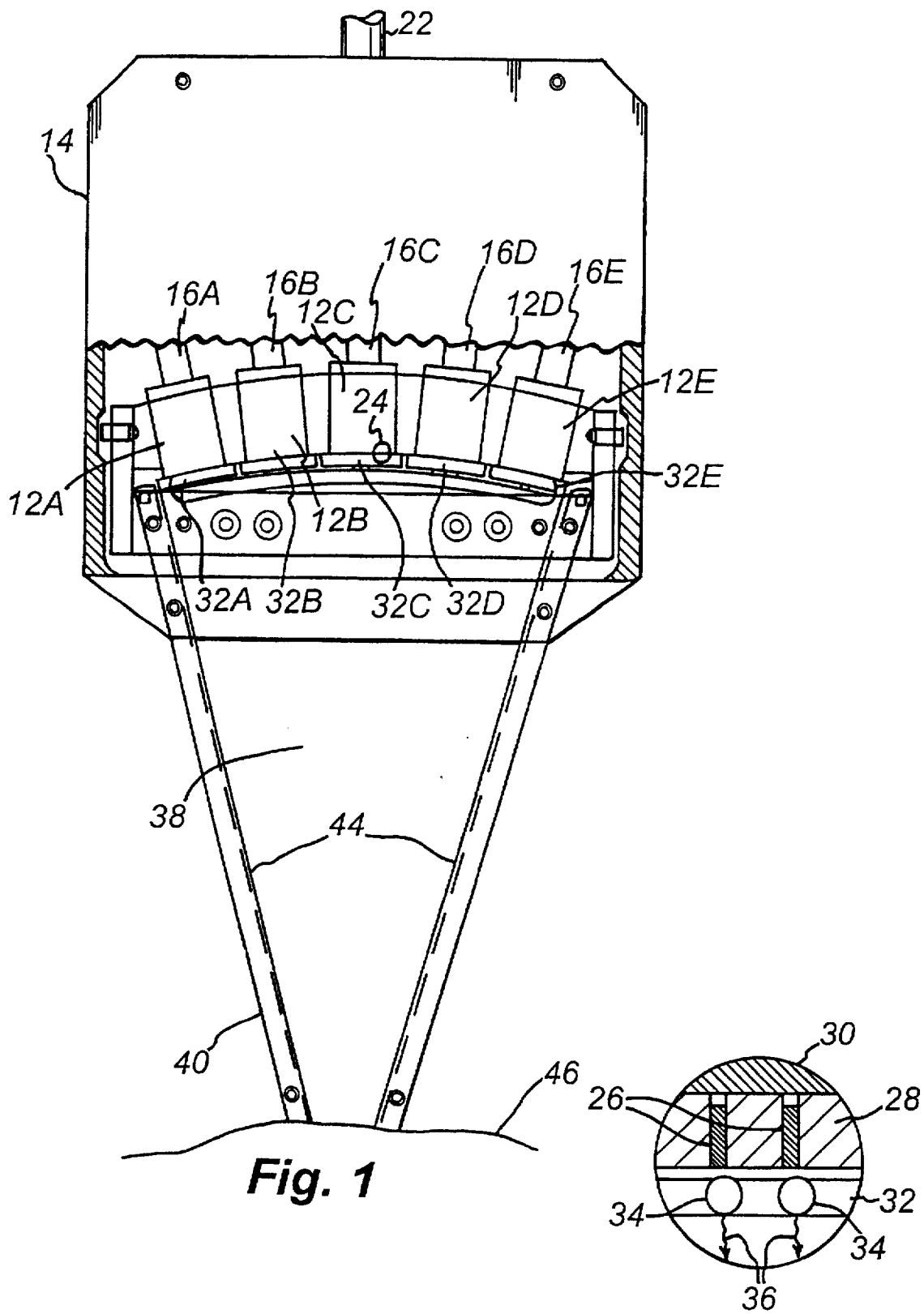
FIG 1 is a side view of a diode laser device in accordance with a preferred embodiment of the invention.
FIG. 2 is an enlarged sectional view of a portion of the diode laser device shown in FIG. 1.

The figures illustrate a diode laser device 10 in accordance with a preferred embodiment of the invention. The device includes five (5) diode laser arrays 12A–12E mounted in a suitable housing 14. The diode laser arrays 12 each have two short pieces of tubing protruding from the rear of each diode array (only one tube 16A–16F per array may be seen in the drawing, with the other tube for each array being behind the tube shown) to provide for the inflow and outflow of water or other coolant. Such coolant enters and exits the housing 14 through tubing 22 and is distributed to each of the arrays in a maimer standard in the art. Similarly, electrical power for the arrays is brought into the housing and distributed to each of the arrays in a conventional manner.

As may be best seen in FIG. 2, which figure is an enlargement of area 24 in FIG. 1, each diode array 12 consists of a plurality of diode laser bars 26 which bars are separated by spacers 28. As indicated earlier, the diode laser bars are an array of individual emitters formed on a single chip or other monolithic structure, which is typically about 1 cm in length, 0.01 cm thick and 0.05 cm deep, with each bar normally containing from approximately 15 to 100 individual emitters along its 1 cm length. Each array 12 may, for example, contain approximately 10 diode bars arrayed in a stack (two bars of such stack being shown in FIG. 2) and a second stack may be provided adjacent to the first (but hidden from view by the stack shown) for a total of 20 diode laser bars 26 for each laser array 12. However, these numbers are for purposes of illustration only and are by no means a limitation on the invention.

As indicated earlier, one problem for high-fluence laser devices is that, when the diode bars are operated for extended durations, not only do they heat, but if there is insufficient spacing between diodes, the capacity of material 28 to remove heat may be exceeded and the heat from the diode bars may interact. It is, therefore, important that spacers 28 between diode bars 26 be of sufficient size so as to prevent interaction between diodes and also that these bars be formed of a material which has both good heat conduction properties and good heat capacity. In particular, these spacers or heat-sinks 28 must be designed to handle the transient heating associated with a long pulse rather than designed for average power operation as is typically done. This is accomplished by utilizing a material for spacers 28 having high-thermal conductivity and high-thermal capacity. Analytical modeling has indicated that the relevant figure of merit of the material is the square root of the thermal conductivity times the thermal heat capacity of the material. In addition, the modeling indicates that the spacing between bars needs to be by a distance corresponding to about one-half the square root of the diffusivity of the material for spacers 28 multiplied by the pulse duration of pulses emitted by laser diode bars 26 in order to minimize bar-to-bar thermal interaction. Suitable materials for spacers 28 include beryllium oxide, cubic boron nitride, diamond, copper and copper tungsten. For bars operating with approximately 30 ms pulses and mounted between copper spacers, the distance between bars would be approximately 1 mm. For bars mounted in beryllium oxide spacers, such material having a lower diffusivity, this distance is less by a factor of approximately 1.6.

Spacers 28 are bonded with a material having good heat transfer properties to a ceramic backplate 30 or to a backplate formed of some other material having high thermal conductivity. The material for backplate 30 may, for example, also be beryllium oxide or some other heat conducting oxide or it could be copper. Backplate 30 is either bonded to a cooler block or itself functions as a cooler block containing tubes or openings through which water or other cooling fluid flowing through projections or tubes 16 may flow. There may be a continuous flow of cooling fluid through these cooler blocks during operation of the device and preferably also before operation of the device to remove heat from spacers 28 and thus from diode laser bars 26.

By providing the heat management mechanisms discussed above, and in particular by using materials for spacers 28 which have high thermal conductivity and heat capacity, operation of the diode laser bars for durations of 30 ms and more can be achieved with modest temperature rise, and even longer duration pulses can be provided, with durations up to 100 ms and beyond, with a temperature rise of no more than 30° C., which is compatible with long life for the diode bars.

A microlens array 32A–32E is mounted adjacent each laser array 12. Each microlens array 32 consists of a glass fiber 34 in front of each diode laser bar 26 in a manner such that light from the diode laser bar enters on one side of the fiber and exits on the opposite side as shown by the lines 36. The fibers 34 are operative to increase the brightness of the array output by reducing divergence of the light from the diode laser bars 26. Ray-trace analysis indicates that with the fiber microlenses attached to the diode laser arrays, the area solid angle product of the array could be decreased by a factor of twenty. If more sophisticated microlens arrays are used, brightness improvements of an additional factor of ten or more could be achieved. Such more sophisticated microlens arrays could include shaped microlenses wherein for example each fiber 34 is flat on one side, or fibers having a radial reflective index gradient (i.e., have a refractive index which varies radially, being smaller at the edges and increasing toward the center). The diameter of the fibers 34 should be slightly less than the spacing of the bars 26. The fibers can be mounted on a frame (typically made from ceramic) or mounted on supports extending from the spacer material. Further, rather than using discrete fibers 34, the microlens array may be formed as a monolithic one- or two-dimensional sequence of "lenslets" formed in or on a translucent material. The material may be a glass or plastic, with several techniques currently being available in the art for forming such monolithic microlens arrays. Monolithic microlens arrays may provide better tolerances and may be less expensive to fabricate, particularly in quantity. It is also possible that some other type of optical device/array could be used for reducing divergence, but microlens arrays are at this time clearly preferred.

The outputs from the microlens array 32 are channeled to a non-imaging condenser 38 contained within a condenser housing 40. Condenser 38 has a generally pyramid-like shape with a generally rectangular opening at its top large enough to receive the outputs from the microlens array 32 and a generally rectangular opening 42 at its bottom which is substantially smaller than the opening at its top. For one embodiment of the invention, which is intended primarily for medical dermatological applications, the opening 42 is a square opening which is 0.8 cm². Condenser 38 may be of a type known in the art including a hollow, non-imaging condenser which has side walls 44 which are mirrored reflective surfaces, for example, polished copper or gold. The condenser 38 may also be of a solid glass material utilizing total internal reflection to transmit light to the exit opening. Other non-imaging (lensless) condensers might also be utilized.

One objective of condenser 38 is to provide an overall decrease in area, which is for example by a factor of 12 or more, with very high efficiency, for example greater than 80 percent. By reducing the illuminated area while maintaining most of the energy, high fluence can be achieved. The non-imaging condenser 38 or other non-imaging approach offers several advantages over a focusing lens for condensing the light into a smaller area. These include:

1) The spot size and shape can be chosen by appropriate design of the condenser; and in particular, the illuminated spot can be easily made square, permitting treatment over much larger areas by sequentially treating adjacent areas.
2) The condenser effectively mixes the light output from the laser arrays through the microlens arrays and thus assures that the beam output is uniform, thereby providing a substantially constant fluence across the illuminated area.
3) The condenser gives a sharp, well-defined beam edge which allows uniform fluence to be applied to adjacent areas.

4) The condenser can be applied directly to the target 46 thus precisely defining the illumination area.

As may be seen from FIG. 1, arrays 12 are mounted along an arc, the radius of which extends from a point determined by extension of the sides of the condenser to a junction or intersection point. This increases the transmission of light energy, with light from the outer diode arrays otherwise suffering greater loss than light from the center diode arrays. While the individual diode arrays 12 could have their emitting surface similarly arced, the incremental advantage in doing this is not normally sufficient to warrant the added cost.

In operation, the device 10, which may for example be hand-held, is placed adjacent target 46 in the area to be treated. While the bottom 42 of condenser 38 may be spaced slightly from target 46, it is preferable that end 42 of the condenser be in contact with the target in the area to be illuminated and, in some applications, pressure may be applied by the device to the target area. If water or other coolant fluid is not already flowing through the diode arrays for cooling purposes, the flow of coolant should be initiated and the diodes then activated for the selected duration. For medical applications, and in particular for certain dermatological applications, a pulse duration of 1 ms to 100 ms might be appropriate with durations of up to 30 ms being more common. Such pulse durations could, with the laser diode bars previously discussed, produce a fluence at the target surface of 10 to 100 J/cm$^2$, well in excess of what has previously been available. Dermatological conditions for which the laser device of this invention might be utilized are discussed in copending application Ser. No. 08/636,286, filed Apr. 23, 1996, entitled METHODS FOR THE LASER TREATMENT OF SUB-SURFACE BLOOD VESSELS and assigned to the assignee of the instant application. However, applications for the diode laser device of this invention are in no way limited to dermatological applications and the device may be utilized for many medical, industrial, research and other applications where a laser having a high fluence output is required/desired.

While the invention has been particularly shown and described above with reference to a preferred embodiment and various modifications thereto have been discussed above, it is to be understood that further changes in form and detail may be made by those skilled in the art without departing from the spirit and scope of the invention and that the invention is only to be limited by the following claims.

What is claimed is:

1. A high fluence diode laser device comprising:
   at least one diode laser array, each array having a plurality of diode laser bars, which bars are separated by spacers formed of a material having both high thermal conductivity and high thermal capacity, said bars being spaced by the spacers by an amount adequate to avoid significant thermal interaction between bars;
   an optical array mounted to receive light energy from the diode bars and to reduce the divergence of light energy outputted therefrom; and
   a non-imaging condenser mounted to receive light energy passing through the optical array and to channel such energy to a smaller area for increased fluence.

2. A device as described in claim 1 wherein said condenser has a truncated pyramid-like shape, with light energy entering the large end of the pyramid and exiting the small end.

3. A device as described in claim 2 wherein said smaller area of the condenser has a generally square shape.

4. A device as described in claim 2 wherein the output from the condenser is applied directly to a target.

5. A device as described in claim 2 wherein the output area of condenser is greater than 0.4 cm$^2$.

6. A device as described in claim 2 wherein the condenser is a hollow non-imaging condenser.

7. A device as described in claim 2 wherein the condenser is a glass total-internal reflecting condenser.

8. A device as described in claim 2 wherein the diode laser arrays are mounted at angles to each other along an arc having a center at the point where sides of the truncated pyramid condenser converge.

9. A device as claimed in claim 1 wherein the optical array is a microlens array.

10. A device as claimed in claim 9 wherein said microlens array is a monolithic sequence of lenslets.

11. A device as described in claim 9 wherein said microlens array is formed of a single glass fiber adjacent each bar and positioned to have light energy from the bar pass through the side of the fiber.

12. A device as described in claim 11 wherein each said glass fiber is shaped to further reduce divergence of light outputted therefrom.

13. A device as claimed in claim 11 wherein the microlens fibers have radial reflective index gradients to further reduce divergence of light outputted therefrom.

14. A device as described in claim 1 wherein the spacing between bars is by a distance corresponding to approximately one-half the square root of the diffusivity of the spacer material times the pulse duration.

15. A device as described in claim 1 wherein the material for the spacers has a relative figure of merit for which the square root of the material's thermal conductivity times the thermal heat capacity of the material is maximized.

16. A device as described in claim 1 wherein the material for the spacer is beryllium oxide.

17. A device as described in claim 1 wherein the material for the spacer is copper.

18. A device as described in claim 1 wherein the diode laser bars operate at a wavelength of from 750 nm to 950 nm.

19. A method for forming a high fluence diode laser device comprising the steps of:
   providing a plurality of diode laser bars mounted in at least one diode laser array having spacers between bars formed of a material having both high thermal conductivity and high thermal capacity, said bars being spaced by the spacers by an amount adequate to avoid significant thermal interactions between bars;
   mounting an optical array to receive light energy from the diode bars and to reduce the divergence of light energy outputted therefrom; and
   mounting a non-imaging condenser to receive light energy passing through the microlens array and to channel such energy to a smaller area for increased fluence.

* * * * *

UNITED STATES PATENT AND TRADEMARK OFFICE
CERTIFICATE OF CORRECTION

PATENT NO. : 5,743,901
DATED : April 28, 1998
INVENTOR(S) : Grove et al

It is certified that error appears in the above-identified patent and that said Letters Patent is hereby corrected as shown below:

On the title page, item [56] U.S. Patent Documents insert the following

U. S. PATENT DOCUMENTS

| EXAMINER INITIAL | PATENT NUMBER | | | | | | | ISSUE DATE | PATENTEE | CLASS | SUBCLASS | FILING DATE IF APPROPRIATE |
|---|---|---|---|---|---|---|---|---|---|---|---|---|
| | 5 | 2 | 5 | 8 | 9 | 8 | 9 | 11/02/93 | Raven | | | |
| | 5 | 3 | 1 | 9 | 5 | 2 | 8 | 06/07/94 | Raven | | | |
| | 5 | 4 | 6 | 3 | 5 | 3 | 4 | 10/31/95 | Raven | | | |

Signed and Sealed this

Ninth Day of February, 1999

Attest:

Attesting Officer

*Acting Commissioner of Patents and Trademarks*